(12) United States Patent
Gittleman

(10) Patent No.: US 7,632,096 B2
(45) Date of Patent: Dec. 15, 2009

(54) ROTATING WINGED LOW PROFILE IMPRESSION TRANSFER CAP

(76) Inventor: Neal B. Gittleman, 50 Briar Hollow La., Suite 150 West, Houston, TX (US) 77027

( * ) Notice: Subject to any disclaimer, the term of this patent is extended or adjusted under 35 U.S.C. 154(b) by 134 days.

(21) Appl. No.: 10/967,546

(22) Filed: Oct. 18, 2004

(65) Prior Publication Data

US 2006/0084033 A1    Apr. 20, 2006

(51) Int. Cl.
*A61C 8/00*    (2006.01)

(52) U.S. Cl. ...................................... 433/173

(58) Field of Classification Search .......... 433/172–176
See application file for complete search history.

(56) References Cited

U.S. PATENT DOCUMENTS 5,055,047 A * 10/1991 Names ........................ 433/214
6,068,478 A * 5/2000 Grande et al. ............... 433/172
6,213,773 B1 * 4/2001 Gittleman .................... 433/172
6,951,460 B2 * 10/2005 Halldin et al. ............... 433/173

\* cited by examiner

*Primary Examiner*—Ralph A Lewis
*Assistant Examiner*—Sunil K Singh

(57) ABSTRACT

An open topped, adjustable wing impression post cap apparatus with a low profile for taking triple tray impressions of upper and lower dentition with the jaw closed. The adjustable winged low profile impression cap has rotating wings to avoid interference with other mouth structures. By aligning a single projection against a matching surface, a low profile, winged impression cap is placed in a unique clocking position over a low profile impression post or an installed implant abutment. The open top low profile allows adjustment of the abutment and impression post retaining hardware. Rotating the wing assembly into a non-interfering, buccal-lingual position allows the complete centric closure of the jaw. Time and material saving triple tray procedures are improved and costs reduced.

5 Claims, 2 Drawing Sheets

ROTATING WINGED LOW PROFILE IMPRESSION TRANSFER CAP

BACKGROUND OF THE INVENTION

The need to save time and improve the accuracy in the preparation of crowns and bridges with implants drives the modern competitive dentist. The dentist takes advantage of the use of the triple tray to speed the taking of simultaneous impressions of the upper and lower dentition and a bite pattern during centric closure. Triple trays cannot be used if standard tall impression posts are used. This invention combines a short impression post and impression cap with a low profile that will not interfere with a complete closure of the jaws. The post and cap have been further refined to a single orientation the to avoid potential mistakes in the lab. Further improvements that allow the repositioning of the perforated retaining wings are the subject of this invention.

In the inventor's prior application Ser. No. 09/828,593 now issued as U.S. Pat. No. 6,508,650, the inventor teaches a low profile, non-interfering dental implant impression cap for making time-saving and accurate, simultaneous upper and lower impressions and bite registration with the jaw accurately positioned in centric closure. Featured in that invention are a number of symmetrical projections or surfaces that allow the choice of several possible clocking positions of the low profile impression cap on the impression post. The inventor feels that this could lead to potential error of communication between the dental surgeon and the lab, resulting in an improperly clocked prosthesis. This invention removes this ambiguity by offering a single clocking orientation in combination with a rotating winged assembly to avoid interference with proximal teeth.

A number of implants in current use, for example, those of the Thommen and Straumann implant systems are adaptable to the a winged low profile impression cap for use with a triple tray, if the following modifications are made. These implant systems have a single clocking position that cannot be dependably determined during implant fixture installation. Rather than offer several winged impression caps with the wings clocked at different angles to avoid surrounding structures in the mouth, a single impression cap with a rotating winged element is offered. Additionally, the impression cap has an open top to allow access to abutment mounting hardware while the cap is in place.

A BRIEF DESCRIPTION OF THE DRAWINGS

Figure 1:
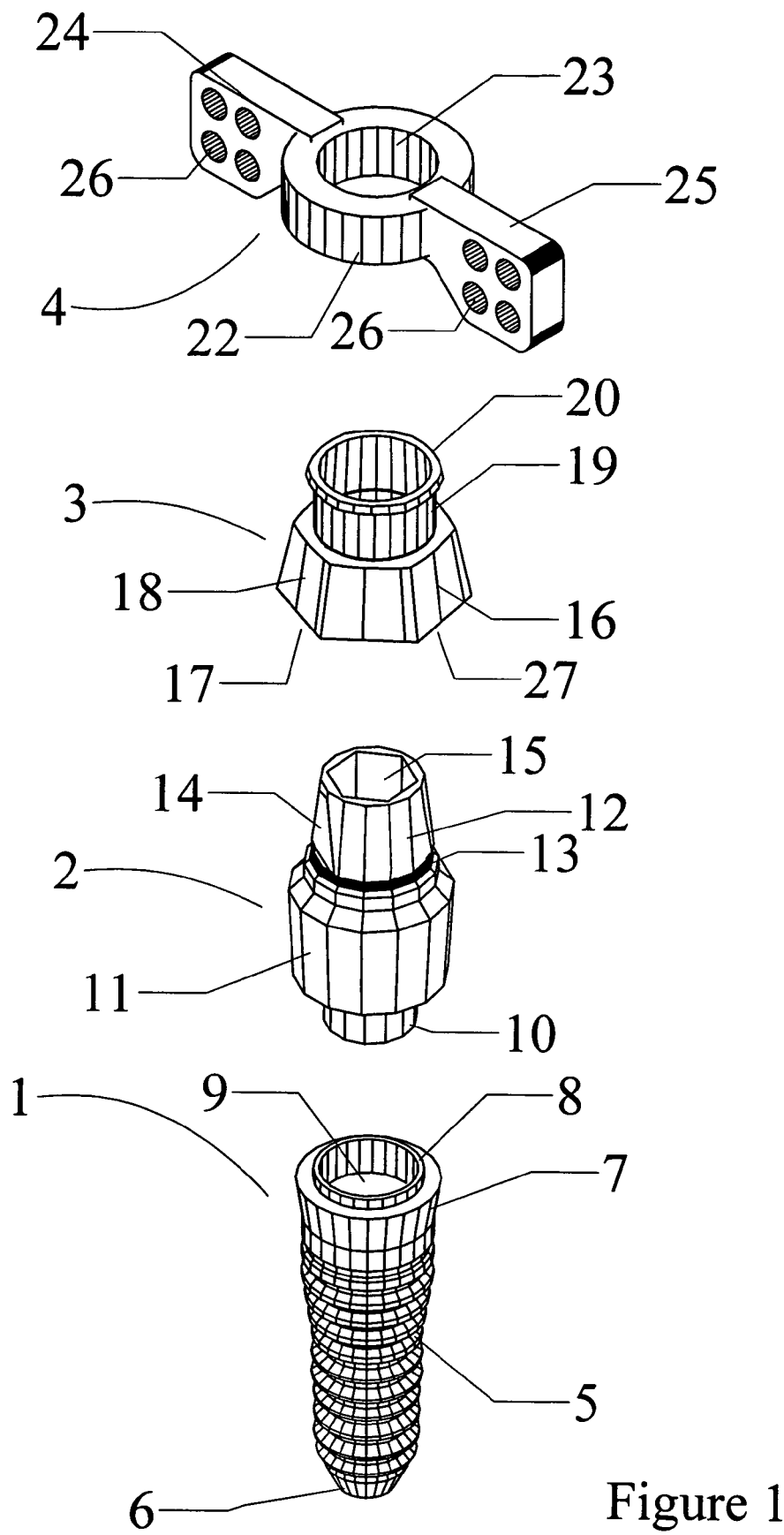
Figure 2:
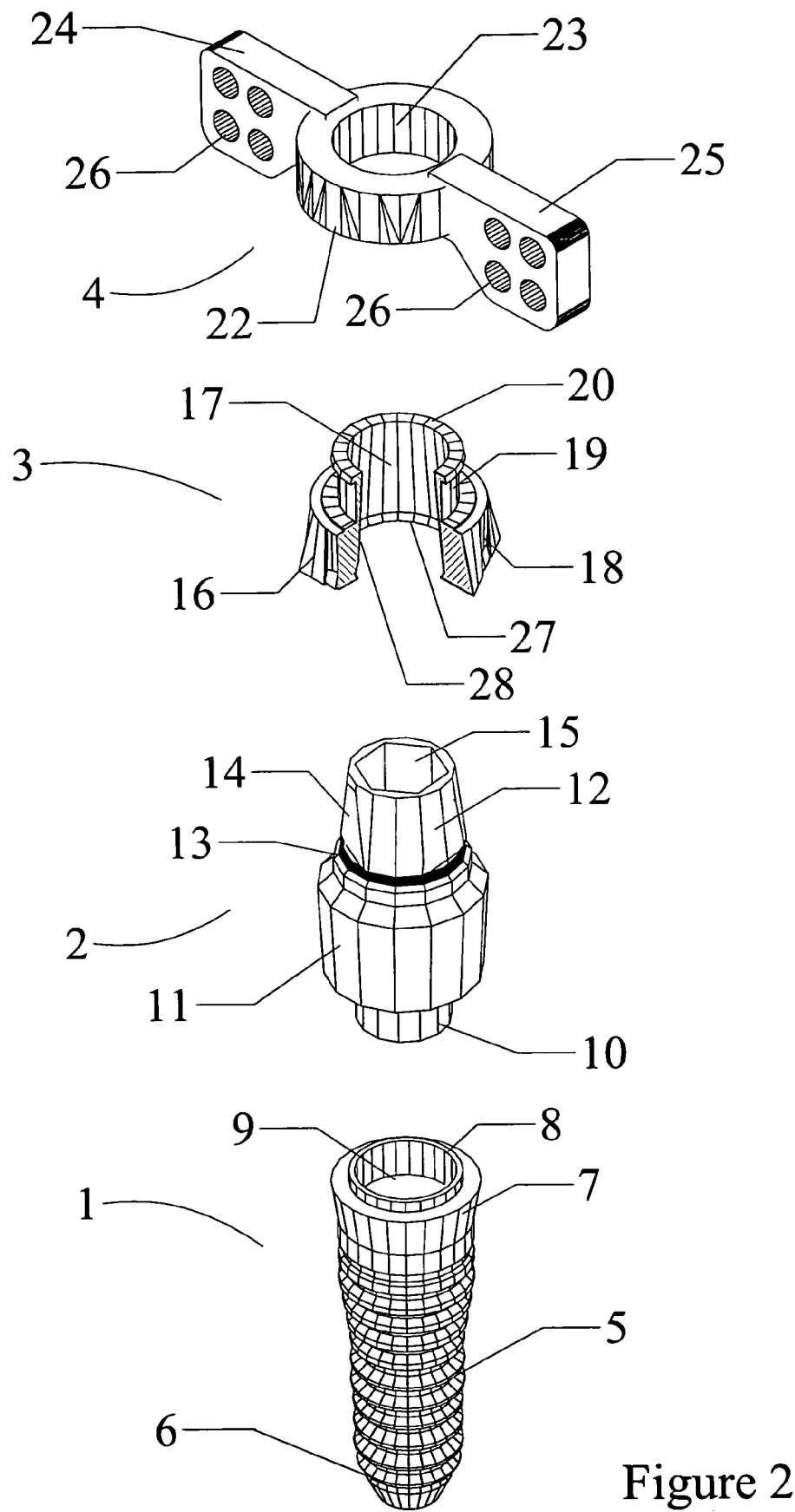

FIG. 1 is a perspective view of a rotating wing, open topped impression post cap; and FIG. 2 is a perspective view of detailed cut-away view of a winged, open topped impression cap.

DETAILED DESCRIPTION OF THE DRAWINGS

In FIG. 1, the titanium implant fixture 1 is equipped with a self-starting thread at distal end 6 and a tapered threaded body 5 having a thread profile intended for immediate loading. The upper end has a flared margin 7 to mimic the emergence profile of a natural tooth. Upper end 8 has a tapered recess 9 with an internal thread (not shown) located within the body of the fixture. Additionally, a deep internal hexagonal region allows for a hexagonal driving wrench to place the fixture within the jawbone. Abutment 2 has a lower tapered projection 10 that matches with the tapered recess 9 in the implant fixture. The abutment is not "clocked" in the implant and can be placed at any radial position. This is convenient with abutments featuring an offset angle for anterior teeth. The abutment 2 has an extension region 11 a tapered upper projection 12 having a circumferential locking groove 13 and at least one flat 14. Current systems tend toward the use of a single flat to clock the abutment to an overlying prosthesis in order to maximize the surface area and grip of the taper 12. Axial through hole 15 allows for an internal screw to hold the abutment to the implant fixture. An upper internal threaded region within recess 15 accommodates the attachment of the final restoration to the abutment. It is possible to lock by means of a taper fit an abutment to an implant with a light tap. A substantial upward parting force is needed to remove the abutment and unlock the taper. In those circumstances where the occlusive forces are only directed axially, the taper will hold best. Offset abutments or those subjected to radial torque forces might rotate loose in a single anterior prosthesis without a flat.

The radial alignment of the flat 14 may not be predictable during installation of the abutment. The perforated wings of the impression cap of the prior art might interfere with proximal teeth, especially with abutments having a single flat. This invention relies upon a snugly fitting, radially adjustable, rotating winged assembly 4 which mates with impression cap 3.

FIG. 2 illustrates that the impression cap 3 has an internal taper 17 that mates with the external taper 12 of the abutment 2. An internal lip 27 within the impression cap snaps into groove 13 of the abutment. The internal taper of the impression cap has a flat projection 28 that mates and clocks with flat 14 on the abutment. Truncated pyramidal faces 16 act to radially lock the impression cap within the impression compound. Grooves, indentations or striations 18 on these external surfaces 16 can increase the holding and positioning of the cap. These surface features or projections along with the winged projections snugly hold the impression cap within the impression compound.

The upper end of the impression cap has a hollow conical projection 19 and a retaining rim 20. Rotating winged assembly 4 has a ringed element 22 with a hollow cylindrical inner surface 23 that snugly fits over cylindrical projection 19 of the impression cap. The ring 22 is snapped over rim 20 and held in place. Conical projection 19 and retaining rim 20 together form a groove to prevent the axial motion of the winged assembly 4. This assemblage allows the wings 24 and 25 to be positioned facio-lingually without interference with the proximal teeth and yet remain low enough not to interfere with centric occlusion while taking a triple tray impression. The wings 24 and 25 are perforated with through holes 26 to aid in retaining the wings in the solidified polymer impression material. The objective is to improve holding strength at better tolerances while maintaining a low profile non-interfering fit in centric occlusion. Frictional forces hold the rotating winged assembly in a chosen radial position on the impression cap. The impression cap has an opening through the top to access abutment retaining hardware.

In another embodiment of the invention, the act of snapping the cap 3 with the winged ring 4 in place over the abutment external taper 12 expands the sleeve 19 of the cap and locks the ring 22 stabilizing the wings in a fixed radial position.

What is claimed is:

1. A dental implant registration apparatus having an impression post with a lower, implant compatible, clocking and locking means; a tapered, truncated, conical upper region having an at least one flat face and a circumferential retaining groove, and a top surface with a counter-sunk, axial through-hole for an implant compatible mounting screw comprising a low profile impression cap with perforated side wings and with a tapered, truncated, conical recess having a single flat projection clocking with a single flat face of the impression post; said low profile impression cap having a circumferential inward projecting ridge snapping into and mating with said circumferential retaining groove in said impression post; and said perforated side wings adjustable in radial alignment upon said low profile impression cap.

2. A dental implant registration apparatus as cited in claim 1 comprising said perforated side wings having a rotating ring mounted in a cylindrical groove on said impression cap.

3. A dental implant registration apparatus as cited in claim 1 comprising said low profile impression cap having projecting surface features retaining said impression cap in an impression compound.

4. A dental implant registration apparatus as cited in claim 1 comprising said low profile impression cap having an open top to provide access to said implant abutment retaining hardware.

5. A dental implant registration apparatus as cited in claim 1 in which said impression post comprises a final abutment used to support a prosthesis.

* * * * *